United States Patent [19]
Treskov et al.

[11] Patent Number: 6,129,436
[45] Date of Patent: Oct. 10, 2000

[54] METHOD AND DEVICE FOR VISUAL EXAMINATION

[76] Inventors: Yakov Treskov; Erena Treskova, both of 2329 Hudson Ter., Apt. B5, Fort Lee, N.J. 07024

[21] Appl. No.: 09/433,052

[22] Filed: Nov. 3, 1999

[51] Int. Cl.⁷ ............................................. A61B 3/08
[52] U.S. Cl. ............................................. 351/201
[58] Field of Search ........................ 351/200, 201, 351/222, 237, 238, 239, 243, 245, 246; 600/558; 434/258

[56] References Cited

U.S. PATENT DOCUMENTS 5,344,324  9/1994  O'Donnell et al. .................... 434/258

*Primary Examiner*—George Manuel
*Attorney, Agent, or Firm*—Boris Leschinsky

[57] ABSTRACT

A method and device allows to instantly determine the critical fusion frequency of a person without changing the routine viewing and lighting conditions. For a personal computer user, a window with running stripes or a blinking dot is projected onto a video monitor over an existing application. Gradual increase of the blinking frequency until the fusion of the test object is used in determining the critical fusion frequency. Provisions are made to adjust individually such parameters as a distance from the monitor, brightness, contrast, color and surrounding lighting which leads to improved vision and increased critical fusion frequency as can be verified by the same method and device once adjustment is complete. In a second embodiment, a series of dots, each blinking with an individual frequency is presented to the person to choose the one appearing non-blinking with the lowest blinking frequency thus defining the critical fusion frequency.

7 Claims, 4 Drawing Sheets

METHOD AND DEVICE FOR VISUAL EXAMINATION

BACKGROUND OF THE INVENTION

1. Field of the Invention

The present invention relates generally to a method and device for visual examination and self-examination of a person in natural everyday settings rather then in a setting of a medical laboratory. In particular, the method and device of the present invention allow for determination of a critical flicker fusion (CFF) frequency as an indicator of the person's physical and neurological condition. The device of the invention may be adapted to be used with a personal computer display or another commonly used monitor screen and as such can be projected over the existing viewing environment.

2. Description of the Prior Art

It is well established that various vision parameters can be used in assessing the general state of a human body. In the functioning of the body's nervous system, for example, data is transmitted between the sensory organs, brain and muscles via frequency-encoded nervous transmissions. Whenever a nerve fires, it must "rest" a while before firing again, which resting, or latency period varies depending on many factors, including physiological state. One way to measure the nerves' ability to conduct signals is to input a known signal varying in frequency over time at a sense organ, and test the brain's ability to detect the signal. A simple example is critical flicker fusion frequency (CFF) or flicker fusion frequency (FFF). A blinking light is typically presented to the eyes, and the blink frequency is increased until the light fuses or appears steady and unblinking. This critical fusion frequency is an indication of the physiological state of the nervous system. If CFF changes, nervous transmission speed may have been affected due to fatigue or other physiological or neurological change occurring at the synapses, thus affecting the ability of a person to properly gather and analyze sensory data. Normal CFF may be in the range between 50 Hz and 70 Hz, depending on several factors, including the portion of the retina which is stimulated. Viewing and lighting conditions during the test play the important role in the results of the CFF test as well.

It is well known that several diseases, i.e., multiple sclerosis, diabetes and glaucoma involve neurological deterioration. Such deterioration can be detected and the status of neurological function can be monitored by use of the CFF test. As a disease having neurological involvement with the optic pathways becomes more severe, the CFF for that person decreases. It is also known that the state of fatigue also reduces the CFF. In addition, the CFF varies due to some other factors such as the time of day, etc.

In the past, stationary or hand-held devices for detecting the critical flicker fusion frequency included mainly a stroboscope-type flickering target light, the frequency of which is adjustable. Typically, a person being tested observes the flickering target light with increasing frequency to the point at which it appears to be continuous, such frequency being that person's CFF frequency.

Prior to that method, a rotating drum with vertical stripes or other well distinguished objects was used for the same purpose. Increasing the speed of rotation would lead to the appearance of a single rotating body at a critical speed which once determined can be used to calculate the CFF. In fact, an argument can be made that this method of CFF determination is more physiologically accurate since a person would experience an object moving by much more frequently than a flashing light.

Examples of various devices for CFF testing can be found in the following U.S. Pat. Nos.: 4,324,460 by Daley; 3,891,311 by Fletcher; 3,814,510 by Adler; 3,737,217 by Haines; 3,424,519 by White, and a Statutory Invention Registration No. H293 by Task. All of these devices provide for CFF testing under defined conditions of viewing and lighting such as the distance from the screen, the brightness, color, and contrast of the flickering image (usually a large dot in the middle of the screen) as well as the level of surrounding light. Also, most of the devices require the person to go to the clinic or other medical office and be assisted by another person to perform the test.

At the same time, it is desirable to be able to perform the test at various times of the day and not to wait a long time before the next test appointment is available because the CFF value may change by then. Frequently, the person working with his computer feels the eye strain after some prolonged time of the computer use. There is a need to objectively assess the vision right at that time in order to either adjust the viewing conditions or determine the need for a break. Some devices (such as described in H293) allow for the instant vision testing while some others do not. But even then, once such factors as the position of the person in front of the monitor or the brightness of the screen change, the CFF reading and analysis may become distorted. There is a need therefore for a method and a device allowing for instant vision examination at the working place without changing the lighting and viewing conditions of the person and the visual settings that surround him.

In addition to the position and distance of the person from the monitor, the very viewing conditions of a particular computer monitor screen with a particular computer application displayed on that screen effect the vision function of a person in a sense that they cause eye strain to a different degree. It is important therefore to determine the CFF for the particular visual situation that the person encounters at a particular time. No testing devices of the prior art are capable of providing for such a testing ability. The need exists therefore for a method and a device allowing for objective visual testing conducted within the scope of routine viewing conditions of a person.

If it is found that the CFF readings have declined as compared either with the normal physiological range or a routine reading for this particular person, the viewing conditions of the monitor screen may be adjusted to allow for better vision and reduce the eye strain. For example, the brightness, contrast or color settings may be used to achieve that change. The need exists therefore for a method and a device allowing the person to determine the optimal viewing conditions and once adjusted to verify the positive effect of the change by determining the CFF value under these new viewing conditions.

Finally, the need exists for a device or a computer program allowing to install the vision examination program as a software application for the use with a personal computer. Such program should allow to address not only all the previous needs, but also to accumulate the vision test data for each individual user, all to be used for determining the trend and warn of a pathological condition.

SUMMARY OF THE INVENTION

Accordingly, it is an object of the present invention to overcome these and other drawbacks of the prior art and to address the above mentioned important scientific and technical challenges by providing a novel method and a device for vision examination allowing for instant determination of such parameters as CFF frequency without changing the viewing or lighting conditions.

It is another object of the present invention to provide a novel method and a device for vision examination allowing for projection of the CFF test onto the computer monitor without changing the viewing conditions such as brightness, contrast, color and surrounding lighting.

It is another object of the present invention to provide a novel method and a device for vision examination allowing for CFF testing at various distances from the test object.

It is yet another object of the present invention to provide a novel method and a device for vision examination allowing for self administering the CFF test under routine viewing and lighting conditions.

It is a further object of the present invention to provide a novel method and a device for vision examination allowing to correct the viewing and lighting conditions should initial CFF frequency be below desirable level and re-verify the CFF frequency after such correction.

Finally, it is a further yet object of the present invention to provide a novel method and a device for vision examination in routine viewing and lighting conditions allowing to accumulate the results of the test over time to determine a possible negative trend of the CFF frequency readings.

According to the method of the invention, the CFF test is administered in routine viewing and lighting conditions for an individual person. The method of the invention is especially easily adapted and can be illustrated in a case of a personal computer user although it can also be used in broader situations especially where some monitor or video display is involved. A person using a computer spends most of the time under a fairly constant viewing and lighting conditions. In fact, only a small variation exists between different computer applications that may change the visual perception of the person. All major factors remain the same, such as the distance from the monitor, surrounding lighting conditions, major monitor parameters such as brightness, color, contrast, etc.

According to the invention, a CFF test object is projected onto the free area of the screen. In a first embodiment, the test object may be realized as a blinking dot or a series of running well defined objects such as vertical stripes. The important advantage of the invention is that the background conditions are preserved so that the test results are instantly applicable to assess the physiological state of the person. After the test object is presented, the frequency of blinking or the speed of stripes movement is gradually increased from an initial frequency known to be lower then the estimated CFF frequency by either a test administrator or by the person himself until the perception of fusion of the objects in a single non-blinking object. At that moment the real CFF is either directly determined from the blinking frequency or alternately, it is calculated from the speed of movement and the distance between the person and the monitor screen.

In a second embodiment, a row of dots blinking with different predetermined frequencies is presented to the person either one at a time or all together. The person is asked then to chose the dot appearing as a non-blinking object with the lowest frequency. This embodiment is simpler to operate but provides the CFF frequency reading at predetermined intervals rather then as a variable parameter as in the first embodiment of the invention.

In a variation of the method, once the CFF frequency has been established it can then be compared either with a physiologically acceptable range of CFF readings derived from a number of people, or with a historical data for the same individual. If a deviation is established, the method of the invention allows for changing individually the viewing or lighting conditions to allow for better viewing of the test object. The CFF test is then repeated to verify that the adjustment was performed correctly. If no adjustment can bring the CFF frequency reading into the acceptable range, the person can be advised to rest and reduce fatigue before continuing work or alternately, it can indicate the onset of a disease.

For a better understanding of the invention, its operating advantages and the specific objects attained by its uses, reference should be made to the accompanying drawings and descriptive matter in which there is illustrated a preferred embodiment of the present invention.

BRIEF DESCRIPTION OF THE DRAWINGS a more complete appreciation of the subject matter of the present invention and the various advantages thereof can be realized by reference to the following detailed description in which reference is made to the accompanying drawing in which.

DETAILED DESCRIPTION OF THE FIRST MOST PREFERRED EMBODIMENT OF THE INVENTION

Figure 1:
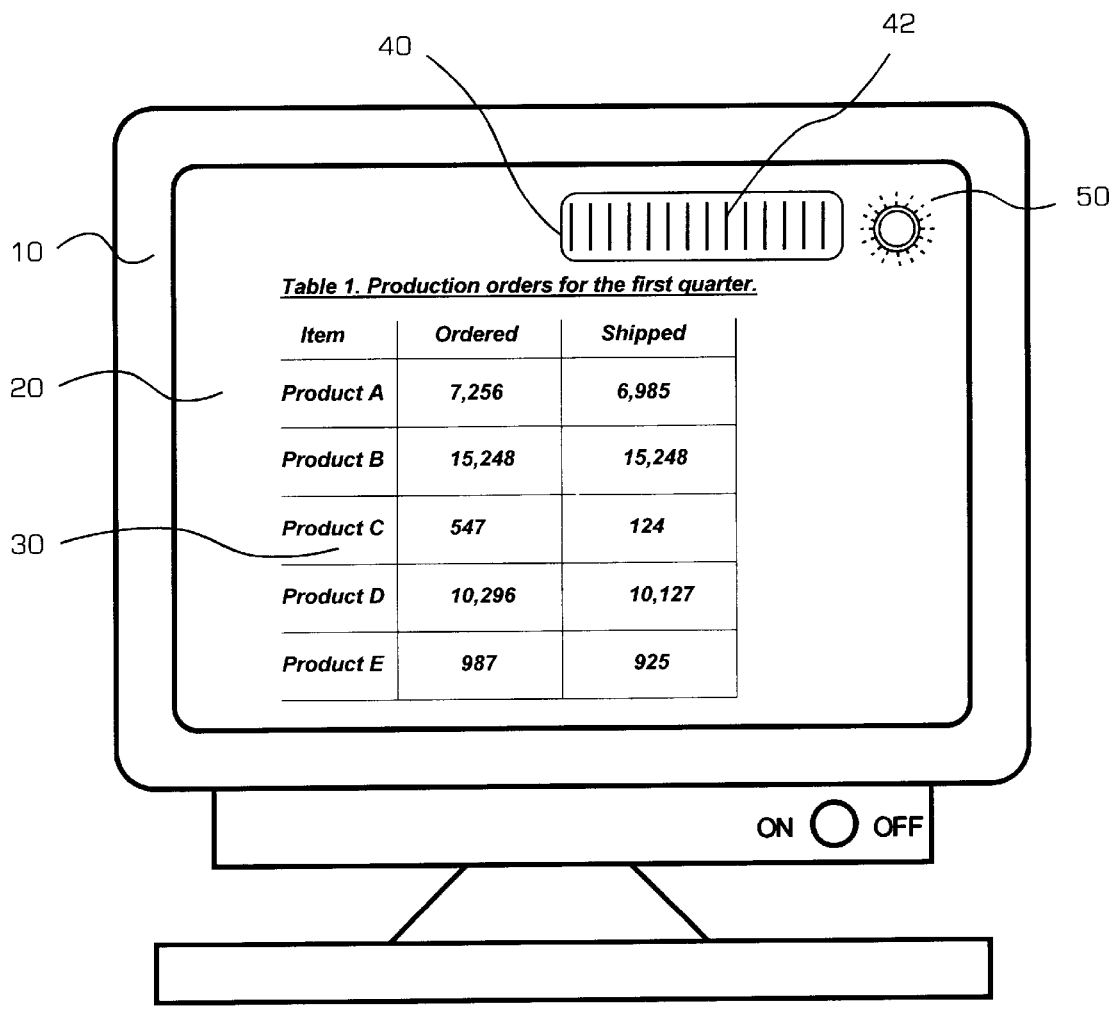
FIG. 1 is a view of a monitor screen with a CFF test occupying a free area of the screen according to the first embodiment of the invention.

A detailed description of the present invention follows with reference to accompanying drawings in which like elements are indicated by like reference numerals.

The method of the invention can be realized as a video display device with appropriate controls or most preferably as a computer program utilizing a broad number of available personal computers.

FIG. 1 shows a typical video display (10) such as a computer monitor with a screen (20) containing a routine application (30), for example a table showing production and shipment results. Those skilled in the art would readily understand that a great variety of other computer applications may be encountered in everyday use which does not change the present invention. Production table (30) is merely one example of such applications.

According to the method of the invention, a visual test object is projected onto any available free area of the screen (20). FIG. 1 shows two alternative test objects: a window (40) with a plurality of running vertical stripes (42) and a blinking dot (50). It should be understood that it is enough to have only one of the two test objects for implementation of the method of the present invention although both can also be used. The choice between the test objects may be up to the person who is using the device. Other test objects can also be used in place of the proposed two without changing the scope of the invention. Once projected on the screen, the frequency of the test object may be controlled in such a way that it is gradually increased until the CFF frequency is determined as described above.

It is not necessary to know the absolute numbers of "normal" CFF readings. The method of the invention can just as well be used for determining the normal CFF range for an individual person and then comparing all further test data to that established level.

It is preferred to determine the initial CFF reading first thing in the morning as it is known to slowly diminish during the day due to normal fatigue.

The most important and distinct feature of the invention is that the test object is projected onto the screen without changing the background parameters of a current computer application. That fact coupled with the same viewing conditions are preserved as defined by the posture of the person, his distance from the screen, the lighting conditions in the room, etc. allows to instantly determine the CFF frequency of the person as applicable to that particular viewing and lighting situation.

Once determined, the CFF frequency reading may be stored in the memory of the computer for further analysis. Such analysis may include comparison with an average CFF frequency as determined for a large number of people, or if the reading has dropped below a predetermined level, a warning to that effect may be issued to the person.

Of course, multiple users can utilize the invention on the same computer by logging in and storing their data individually for further analysis.

Figure 2:
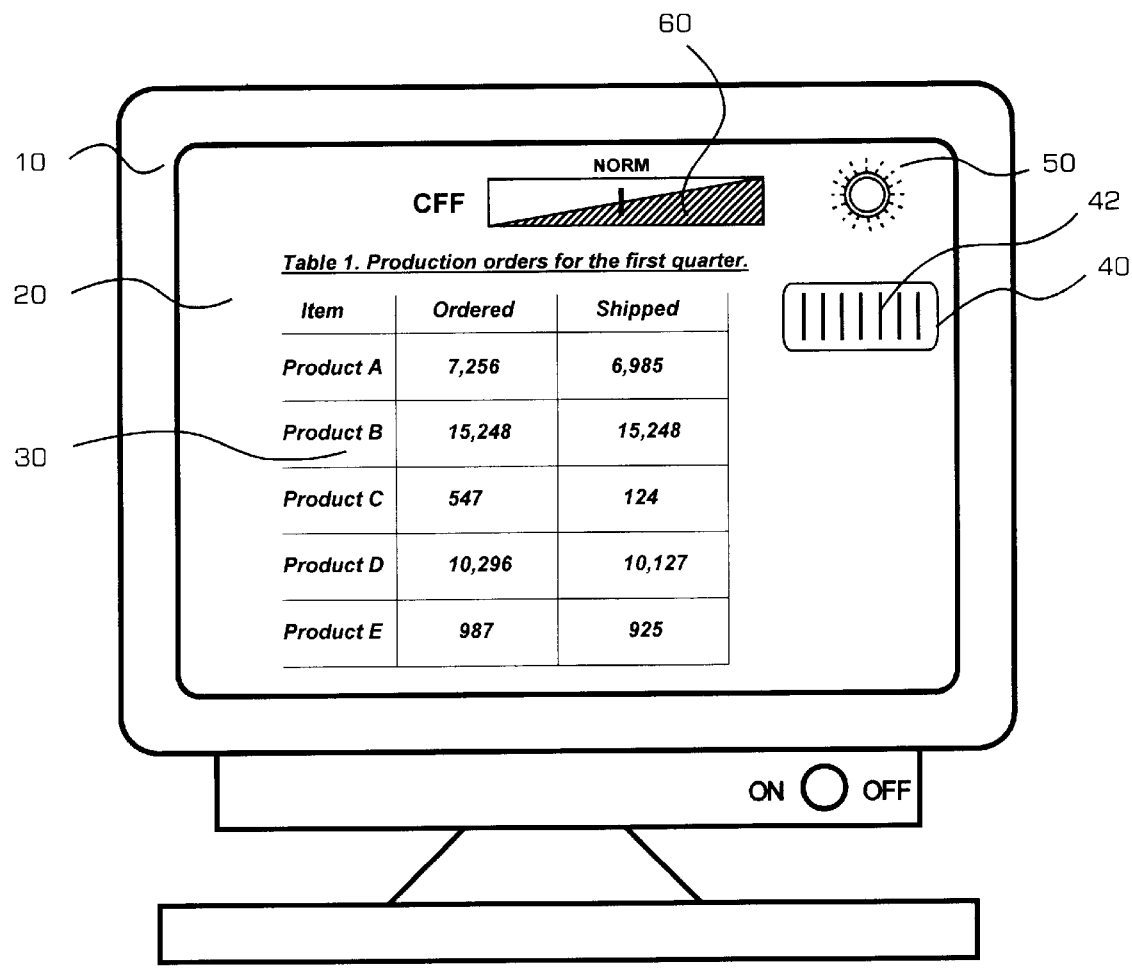
FIG. 2 is a variation of the first embodiment in which the CFF frequency control is also displayed on the screen of the monitor.

FIG. 2 illustrates a variation of the present invention in which in addition to projecting either one of the alternate test objects, the window (40) with running stripes (42) or the blinking dot (50), a frequency control (60) is also represented on the screen so it is more convenient for the person to self administer the test. A normal range of CFF frequency may optionally be displayed on the CFF control window.

In another variation of the invention, the CFF test may be administered while positioning the person at various distances from the screen. As was indicated above, the running stripes method is believed to be closer physiologically to the everyday observations of a person. It is believed to simulate better such situations as a view from a running train or an automobile, or any other situation in which a moving object is observed at various distances from a person. In that case, the ratio of the linear speed V of the running stripes (42) to the known distance R from the person to the screen determines the CFF frequency as can be easily calculated by the computer and as is evident from the following equation:

$$CFF=KV/R,$$

where

CFF is the Critical Fusion Flicker frequency;

V is the linear speed of the moving stripes;

R is the distance between the person and the monitor; and

K is a cumulative factor taking into account physiological conditions of a person as well as the viewing and lighting conditions for the test.

Previous research indicates that the normal range of CFF is about 50 to 70 Hz. Assuming the ratio of V/R of about 1 and ranging between 0.5 to 1.5, one can calculate the value of K as being proportional to the ratio of (50 to 70) over (0.5 to 1.5). Once K is determined for a particular individual, the above equation may be used in reverse to determine the distance from a moving object.

Figure 3:
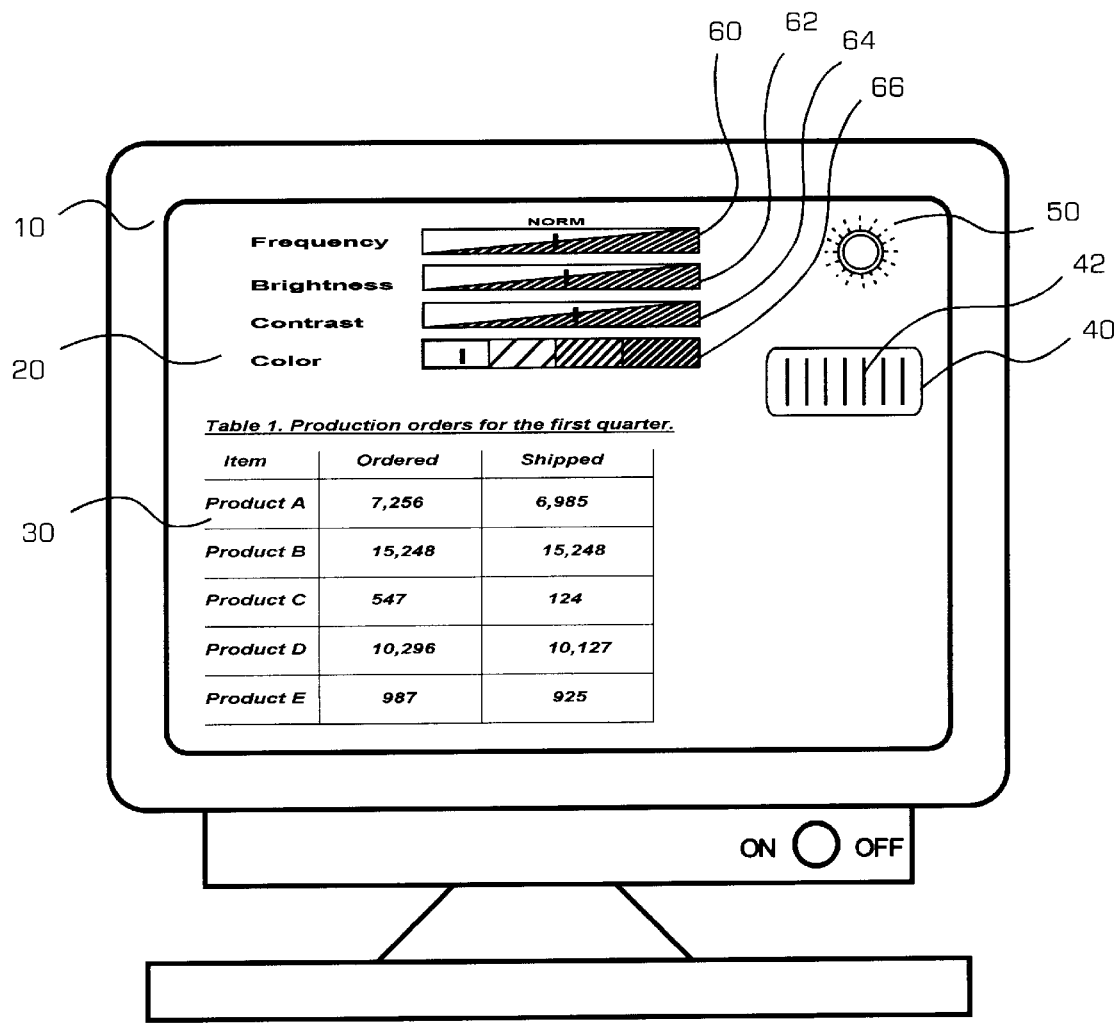
FIG. 3 is a further variation of the first embodiment in which in addition to frequency control, the control of brightness, contrast, and color are also displayed in a free area of the screen, and finally

FIG. 3 shows a further variation of the first embodiment of the invention in which additional controls are provided to change the viewing conditions of the screen and hence the test object. Among these additional controls, the most important are the control of brightness (62), contrast (64), and color (66) (color control is shown on FIG. 3 as the shades of black). That variation of the device and method of the present invention allows to correct the viewing conditions of the test object and of course of the primary routine application projected on the screen should it be determined from the initial CFF test that the reading is below the expected level. Once that fact has been established, an individual adjustment of any of the above mentioned controls in addition to adjusting the surrounding lighting may be undertaken to improve the viewing conditions. Once adjusted, the CFF test can be repeated to verify that the conditions are optimal for continuing work. In case that can not be achieved, the person may be advised to take a break or to consult a physician since an onset of a pathological condition may cause this result. Once the viewing conditions are adjusted and the CFF reading has been verified, the same viewing conditions are maintained when the person is going back to his work which allows for working in optimal viewing conditions.

Another aspect of this variation is that instant and historical analysis of CFF and the underlying test conditions may be undertaken once enough data is accumulated. For example, not only deviation of CFF readings may be determined, but also the extent of correction of individual control parameters or their combination needed to restore the CFF readings to normal levels.

Deviations from the normal levels can be displayed either in absolute numbers or as a percentage of the norm, as preferred by the person administering the test.

The method of the present invention is so simple and available for many people that it can be viewed in line with other common home tests such as checking temperature, blood pressure, pulse, blood glucose and alike.

DETAILED DESCRIPTION OF THE SECOND MOST PREFERRED EMBODIMENT OF THE INVENTION

Figure 4:
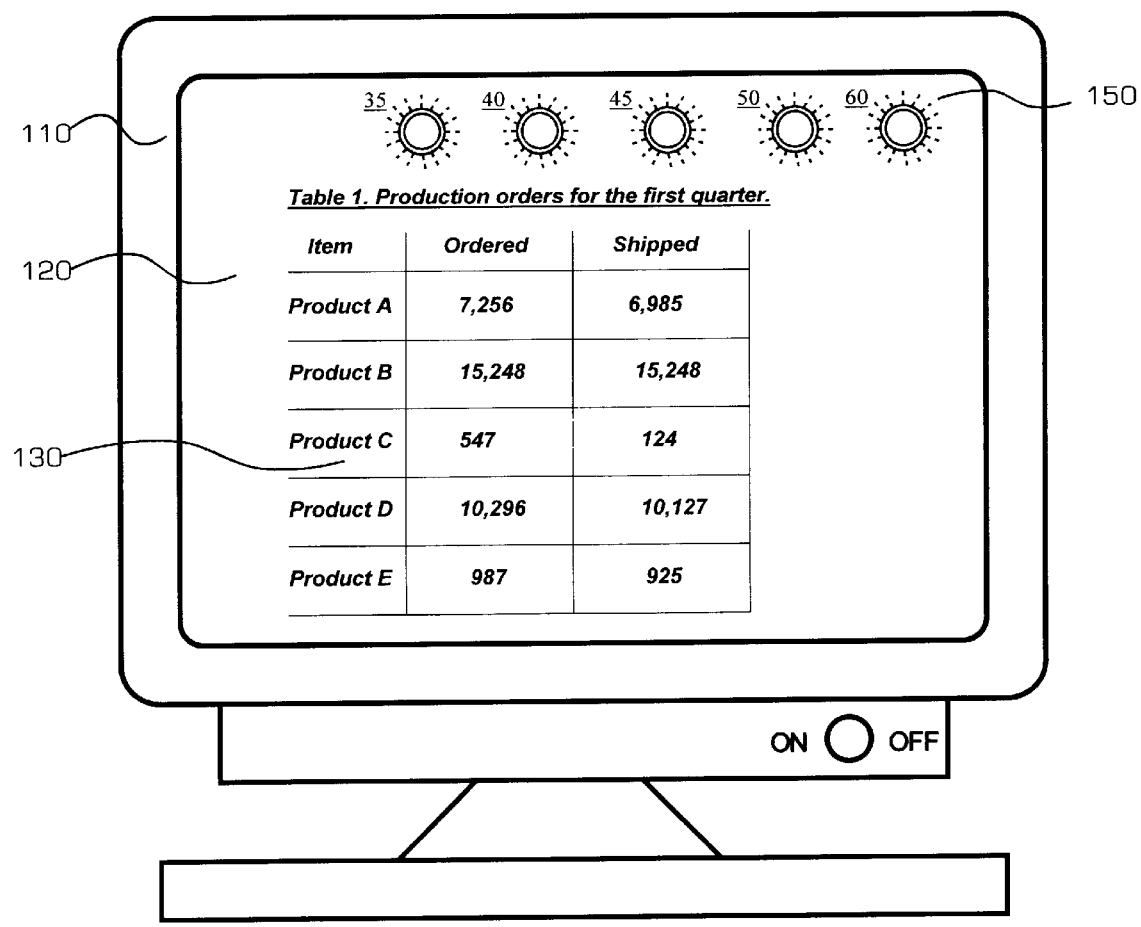
FIG. 4 is a view of the CFF test projected onto a free area of the monitor screen according to the second embodiment of the present invention.

FIG. 4 illustrates the second embodiment of the present invention which is believed to be even simpler to use by an average person. Here, in place of a single blinking dot with variable frequency control, a plurality of blinking dots (150) are projected onto a free area of the screen (120) of the monitor (110) away from the current application (130). Each individual dot is blinking with increasing frequency which is constant and shown next to the dot. The range of these frequencies is selected to cover the normal or expected range of CFF frequency. All dots can be made to blink all at the same time with their respective frequencies or alternately, they cab be turned one by one with a predetermined interval. The person has to choose the dot with the lowest blinking frequency which still appears as a single non-blinking entity. The frequency of blinking associated with this dot is then assigned as a resultant CFF frequency.

A similar situation may be created with a number of windows having vertical stripes or other clear objects running with various speeds individually defined and displayed for each window (not shown).

The advantage of the second embodiment is the simplicity of use, while the limitation is that the accuracy of CFF test is determined by the number of projected test objects. The more the number of blinking dots is, the more accurate the test results will be.

As it can be readily appreciated by those skilled in the art, all variations described for the first embodiment of the present invention are also applicable to the second embodiment with appropriate modifications. An example of such a variation is providing individual control for brightness, contrast, and color. Also, all analysis principles described above are also applicable in the case of the second embodiment of the invention.

In a further variation of the second embodiment not shown on the drawings, the plurality of blinking dots may be realized as a separate light strip or light string equipped with a corresponding number of lamps or light emitting diods and optionally powered by batteries for improved mobility. In that case, it is easy to place that strip in a field of view of a person even if he is not working with a video monitor of some kind. Provided that appropriate means of frequency control are available, the method of the invention may be practiced in a wide variety of situations.

Although the present invention has been described with respect to a specific embodiment and application, it is not limited thereto. Numerous variations and modifications readily will be appreciated by those skilled in the art and are intended to be included within the scope of the present invention, which is recited in the following claims.

What we claim is:

1. A method for instant visual examination to determine critical fusion frequency of a person, said person being in routine viewing and lighting conditions, said method comprising the steps of:

providing a visual test object and a video monitor for viewing said visual test object by said person without changing the routine viewing and lighting conditions; said conditions being defined by a distance between said person and said video monitor, levels of brightness, contrast, and color of said video monitor, as well as surrounding lighting; said test object being presented at a predetermined initial frequency, said initial frequency being lower than an estimated critical fusion frequency;

increasing said initial frequency of said visual test object until a frequency at which a perception of fusion of said visual test object is reported by said person, declaring said frequency the critical fusion frequency for said person in said viewing and lighting conditions, adjusting said distance, brightness, contrast, color, and surrounding lighting to improve said viewing and lighting conditions, and repeating all previous steps until a predetermined desired critical fusion frequency is achieved.

2. The method as in claim 1, wherein said visual test object comprising a window with plurality of running vertical stripes.

3. The method as in claim 1, wherein said visual test object comprising a blinking dot.

4. A method for instant visual examination to determine critical fusion frequency of a person, said person being in routine viewing and lighting conditions, said method comprising the steps of:

providing a visual test object and a video monitor for viewing said visual test object by said person without changing the routine viewing and lighting conditions; said conditions being defined by a distance between said person and said video monitor, levels of brightness, contrast, and color of said video monitor, as well as surrounding lighting; said test object comprising a plurality of dots, each dot blinking at a predetermined individual constant frequency defining a range of blinking frequencies, said range covering an estimated range for critical fusion frequency;

selecting the lowest of said individual frequencies for which a perception of fusion of said corresponding blinking dot is reported by said person, declaring said frequency the critical fusion frequency for said person in said viewing and lighting conditions, adjusting said distance, brightness, contrast, color, and surrounding lighting to improve said viewing and lighting conditions, and repeating all previous steps until a predetermined desired critical fusion frequency is achieved.

5. A device for instant visual examination to determine critical fusion frequency of a person, said person being in routine viewing and lighting conditions, said device comprising:

a video monitor for providing a visual test object for viewing by said person without changing the routine viewing and lighting conditions; said conditions being defined by a distance between said person and said video monitor, levels of brightness, contrast, and color of said video monitor, as well as surrounding lighting; said test object being presented at a predetermined initial frequency, said initial frequency being lower than an estimated critical fusion frequency; and a control means for increasing said initial frequency of said visual test object until a frequency at which a perception of fusion of said visual test object is reported by said person, said frequency defining the critical fusion frequency for said person in said viewing and lighting conditions, said control means including individual control means for adjusting said brightness, contrast and color, whereby when coupled with adjustment of said distance and said surrounding lighting, said control means causing improvement of said viewing and lighting conditions, and increase in critical fusion frequency to a predetermined desired level.

6. A device for instant visual examination to determine critical fusion frequency of a person, said person being in routine viewing and lighting conditions, said device comprising:

a video monitor for providing a visual test object for viewing by said person without changing the routine viewing and lighting conditions; said conditions being defined by a distance between said person and said video monitor, levels of brightness, contrast, and color of said video monitor, as well as surrounding lighting; said test object comprising a plurality of dots, each dot blinking at a predetermined individual constant frequency defining a range of blinking frequencies, said range covering an estimated range for critical fusion frequency; the critical fusion frequency being determined by selecting the lowest of said individual frequencies for which a perception of fusion of said corresponding blinking dot is reported by said person; and a control means for individually adjusting said brightness, contrast, and color;

whereby when coupled with adjustment of said distance and said surrounding lighting, said control means causing improvement of said viewing and lighting conditions, and increase in critical fusion frequency to a predetermined desired level.

7. A computer program for instant visual examination to determine critical fusion frequency of a person, said person being in routine viewing and lighting conditions on a personal computer with a video monitor, said program comprising:

a means for projecting a visual test object for viewing by said person on said monitor without changing the routine viewing and lighting conditions; said conditions being defined by a distance between said person and said video monitor, levels of brightness, contrast, and color of said video monitor, as well as surrounding lighting; said test object being presented at a predetermined initial frequency, said initial frequency being lower than an estimated critical fusion frequency; and a control means for increasing said initial frequency of said visual test object until a frequency at which a perception of fusion of said visual test object is reported by said person, said frequency defining the critical fusion frequency for said person in said viewing and lighting conditions, said control means including individual control means for adjusting said brightness, contrast and color;

whereby when coupled with adjustment of said distance and said surrounding lighting, said control means causing improvement of said viewing and lighting conditions, and increase in critical fusion frequency to a predetermined desired level.

* * * * *